United States Patent
Bolduan et al.

[11] Patent Number: 6,055,060
[45] Date of Patent: *Apr. 25, 2000

[54] ANALYTICAL SYSTEM WITH MEANS FOR DETECTING TOO SMALL SAMPLE VOLUMES

[75] Inventors: Franz Bolduan; Bernd Eisenbarth, both of Mannheim; Karl Miltner, Frankenthal; Helmut Leininger; Detlef Thym, both of Mannheim, all of Germany

[73] Assignee: Boehringer Mannheim GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/895,368

[22] Filed: Jul. 16, 1997

[30] Foreign Application Priority Data

Jul. 16, 1996 [DE] Germany .............................. 196 28 562
Jul. 26, 1996 [DE] Germany .............................. 196 30 160

[51] Int. Cl.$^7$ ................................................. G01N 21/00
[52] U.S. Cl. .......................... 356/433; 356/435; 356/436; 356/39; 356/446
[58] Field of Search ..................................... 356/432, 433, 356/434, 435, 436, 445, 446, 448, 39, 36, 37, 427

[56] References Cited

U.S. PATENT DOCUMENTS

| | | | |
|---|---|---|---|
| 4,755,058 | 7/1988 | Shaffer | 356/446 |
| 5,114,350 | 5/1992 | Hewett | 435/288 |
| 5,234,813 | 8/1993 | McGeehan et al. | 435/7.9 |
| 5,590,052 | 12/1996 | Kopf-Sill et al. | 364/498 |

FOREIGN PATENT DOCUMENTS

| | | |
|---|---|---|
| 0 165 535A2 | 12/1985 | European Pat. Off. . |
| 0 469 377A2 | 2/1992 | European Pat. Off. . |
| 0 732 578A2 | 9/1996 | European Pat. Off. . |

*Primary Examiner*—Hoa Q. Pham
*Attorney, Agent, or Firm*—Nikaido, Marmelstein, Murray & Oram LLP

[57] ABSTRACT

Analytical system for evaluating test elements having means of determining whether a sufficient amount of sample liquid was evenly applied to an application zone comprising in a first embodiment of the invention at least two sources of light which illuminate separate or at least not fully overlapping areas of the application zone or the evaluation zone of the test strip, a control unit with which the light sources, of which there at least two, can be independently activated, at least one sensor which detects light reflected by the evaluation zone or transmitted by the evaluation zone and supplies an output signal proportional to the intensity of light as well as an evaluation unit which receives a first output signal from the sensor and converts it into a first measured value when the first of the light sources is activated, receives a second output signal from the sensor and converts it into a second measured value when the second of the light sources, is activated and compares the measured values and determines whether the deviation of the first value measured from the second value measured is sufficiently small. In a second embodiment of an analytical system according to the invention, at least one light source is used to illuminate the sample application zone or the evaluation zone of a test element and at least two sensors detect light reflected or transmitted by the evaluation zone, the output signal of the sensors being converted into measured values by the evaluation unit which determines whether the deviation of the measured values is sufficiently small.

29 Claims, 11 Drawing Sheets

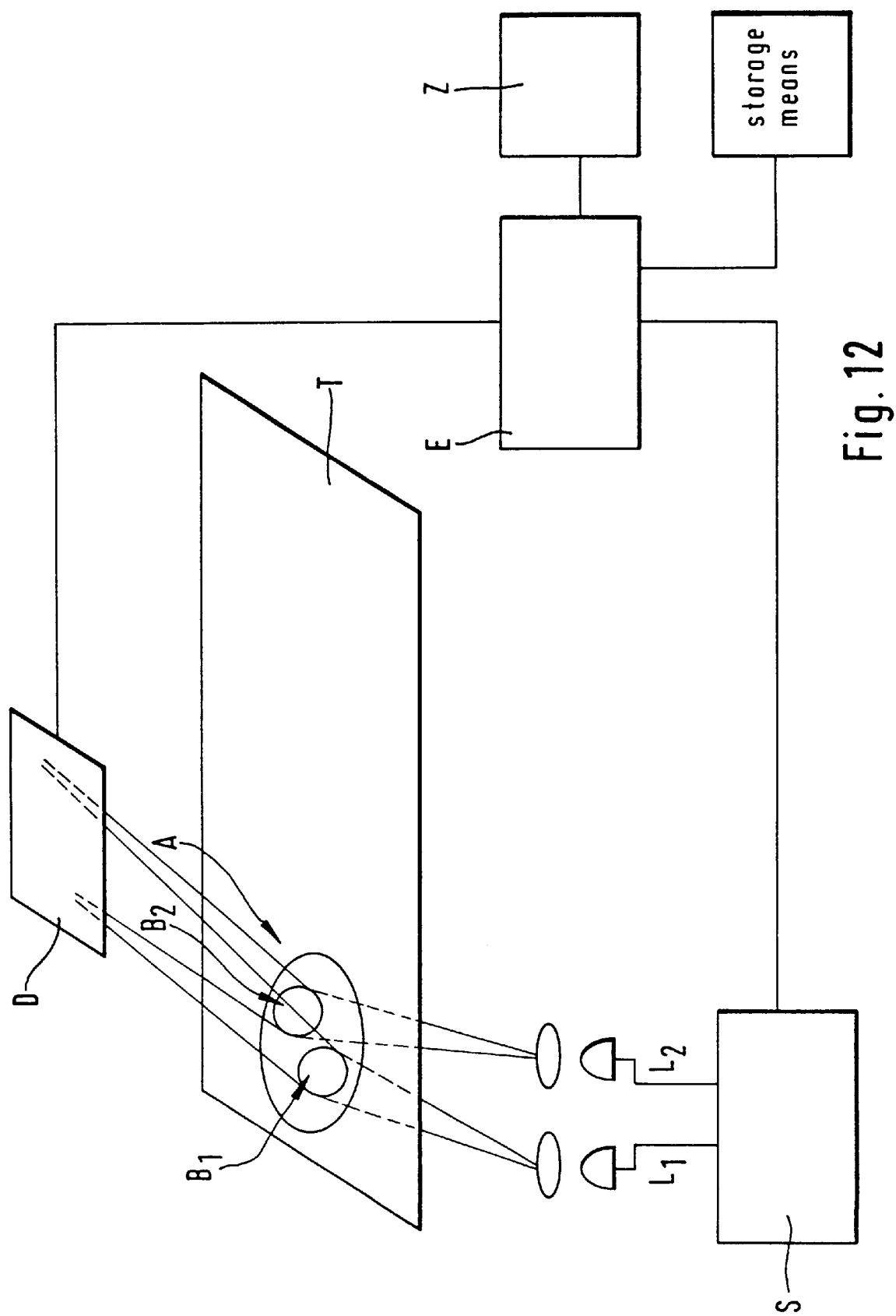

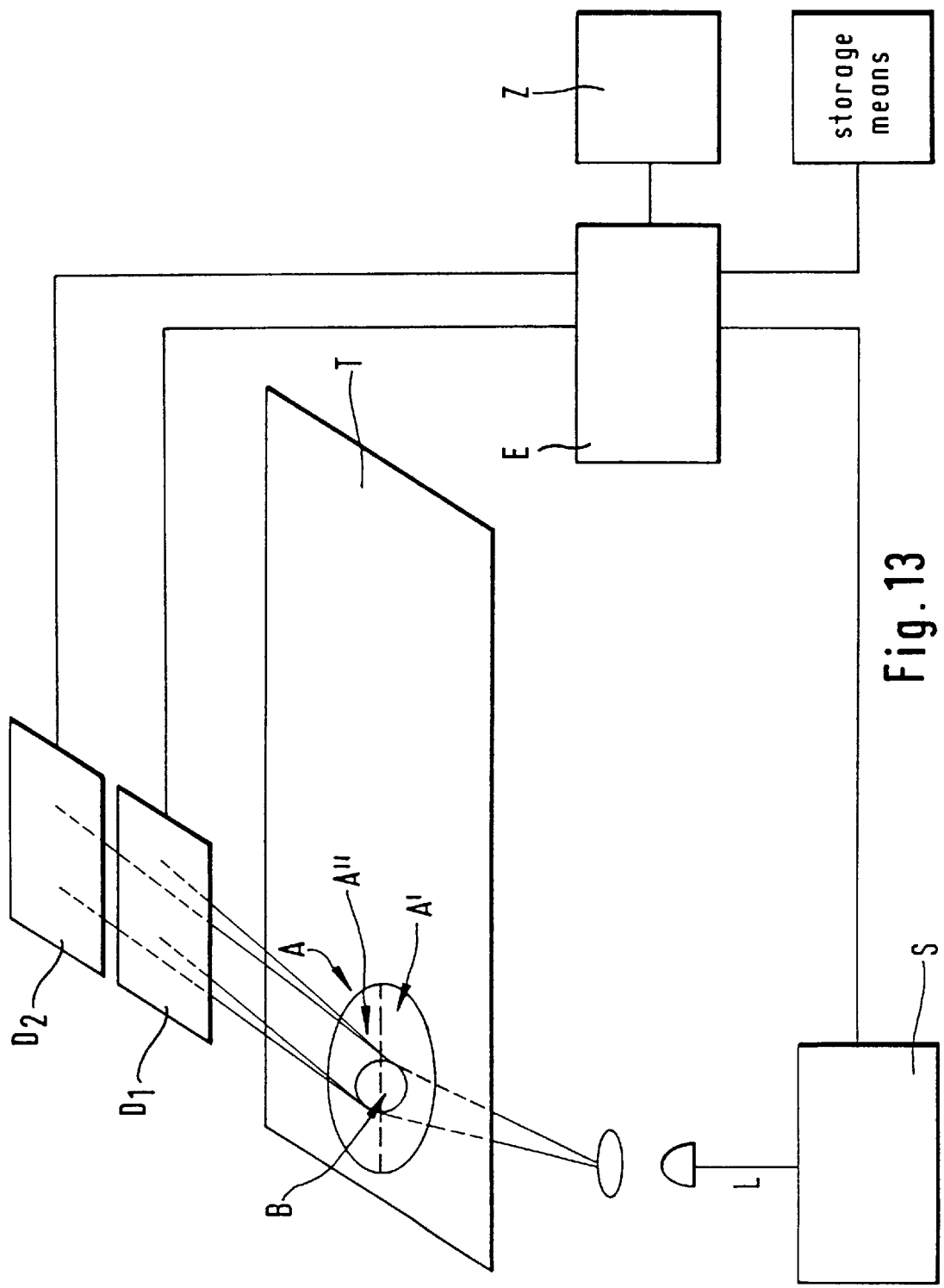

ANALYTICAL SYSTEM WITH MEANS FOR DETECTING TOO SMALL SAMPLE VOLUMES

BACKGROUND OF THE INVENTION

1. Field of the Invention

This invention relates to an analytical system for evaluating test elements having means of determining whether a sufficient amount of sample liquid was evenly applied to a test element application zone. To this end, a first embodiment of the invention comprises of a control unit for activating at least two sources of light independently from each other, wherein said light sources illuminate separate or at least not fully overlapping areas of the application zone of the evaluation zone of the test element. Light reflected by the evaluation zone or transmitted by the evaluation zone is detected by at least one sensor which generates an output signal proportional to the intensity of light. An evaluation unit receives a first output signal when the first of the light sources of which there are at least two is activated and receives a second output signal when the second of the at least two light sources is activated. The output signals are converted by the evaluation unit into measured values and the measured values are compared with each other. When the deviation of the first measured value from the second measured value is sufficiently small, a sufficient amount of sample liquid has been applied to the test element. If the deviation exceeds a preset threshold value, then the amount of sample was either too small and/or was incorrectly applied and the analytical system gives an error warning.

2. Description of the Related Art

In the prior art the problem of test elements generating erroneous results when either too little sample liquid is applied to a test element or when the sample liquid is incorrectly, i.e. not fully applied to predetermined sites has been known for a long time. In the past the user himself has to visually monitor whether the sample liquid was applied to the correct site in sufficient quantity. Visual monitoring by the user is however of poor reliability, particularly for test elements for determining blood glucose levels as used by diabetics whose sight is often impaired by the disease. To solve the said problem, an apparatus is described in the European Patent EP-B-0 087 466, which estimates on the basis of the absorption of water in the infrared region of the electromagnetic spectrum whether the amount of sample is sufficient. The suggested apparatus is however disadvantageous for a portable system such as for example for the measurement of glucose in blood because in addition to the means required for quantitative evaluation, an infrared transmitter and receiver are necessary. Furthermore, the apparatus described in EP-B-0 087 466 performs an integral examination to determine whether a sufficient amount of sample liquid has been applied. For the performance of analytical tests using test elements however not only the total amount of test liquid is of importance but rather also the distribution of sample liquid over the sample application zone. Using this apparatus such cases can not be easily identified in which sufficient sample liquid has been applied but has been unfavorably positioned such that the reagent area of the test element is unevenly or incompletely wetted with sample liquid.

SUMMARY OF THE INVENTION

The object of this invention was to suggest an analytical system which comprises means by which insufficient amounts of sample or an unsuitable application of the sample on the test strip can be recognized with certainty. A further object of the present invention was to suggest means by which insufficient amounts of sample could be identified which can be simply and in an economically feasible manner integrated into a compact analysis system or which are already present in analytical systems.

The above-mentioned object of the invention is solved by an analytical system for the evaluation of test elements which has at least two light sources capable of illuminating separate or at least not fully overlapping areas of the application zone or the evaluation zone of the test element as well as a control unit with which at least two light sources can be activated independently of each other, at least one sensor which detects light reflected by the evaluation zone or transmitted by the evaluation zone generating an output signal proportional to the intensity of the light as well as an evaluation unit which receives a first signal from the sensor and converts it into a first measured value when the first of the at least two light sources is activated and which receives a second output signal from the sensor and converts it to a second measured value when the second of the at least two light sources is activated and also compares the measured values determining whether the deviation between first and second measured value is sufficiently small.

Analogously, in accord with the invention, an analytical system for evaluating test elements is proposed which consists of at least two sensors which detect light reflected or transmitted by respectice areas of the application zone or the evaluation zone and supply an output signal proportional to the intensity of light whereby said areas are separate from each other or are at least not fully overlapping as well as at least one source of light, which illuminates the sample application zone or the evaluation zone, an evaluation unit which receives an output signal from the first sensor and converts it to a first measured value and receives an output signal from the second sensor and converts it into a second measured value and compares the first and second measured values determining whether the deviation of the measured values is sufficiently small.

Analytical systems for the evaluation of test strips are on the one hand employed in the field of clinical diagnostics where it is of importance to achieve high sample throughputs. On the other hand such analytical systems are however also employed in the field of home-monitoring whereby the patient himself is then enabled to perform routine measurements such as blood glucose measurements or determine the coagulative properties of their blood with the aid of suitable test elements and a compact analytical system. In the field of glucose monitoring in particular, analytical systems for the evaluation of test elements have established themselves well. The reason for this is that overly high or excessively low blood glucose levels in diabetics can lead to irreversible physiological damage. For such instruments especially, which are used by large sections of the population (but also for automatic clinical analyzer systems), it is important that a sufficient amount of sample liquid, usually blood, urine or saliva or the like are applied to a predetermined zone of a test element in a suitable fashion. The necessity of the requirement that a certain minimum amount of sample should be applied and that the sample should be suitably positioned becomes clearer when the method of functioning of test elements and their automatic evaluation becomes apparent.

Test elements for analytical evaluation are usually strip-shaped. A reagent layer is usually located on a holder for the purposes of easy handling. The reagent layer reacts with sample, undergoing a detectable change. In many such methods of analytical methods, the detectable change is usually a color change in the visible region of the electromagnetic spectrum. Such a method of analysis is for example described in EP-A-0 354 441. In the determination of coagulation factors in blood however, the interaction of the test element in a magnetic field is examined for example. Furthermore, test elements are known whose fluorescence characteristics change depending on the concentration of the analyte in the sample. This invention is not limited to the application of a given specific method of analysis even although their application in reflection photometry is particularly favorable.

Analytical test elements have the advantage over clinical analyses performed in the liquid phase that an exact dosage of the sample liquid does not have to be executed but rather only an amount within certain limits has to be used. This favorable characteristic of test elements can be explained by reference to their construction. The sample is first applied to an absorbent layer which absorbs a limited volume of sample liquid and gives this up to the reaction zone. The reaction zone comes into contact with a predetermined amount of sample liquid such that quantitative evaluation is possible. If the amount of sample applied to the test strip is too large, this is not taken up by the reaction zone due to its limited absorption capacity and hence cannot lead to false analytical results. This advantageous behavior of analytical test elements is described in EP-A0 345 781.

If in contrast an amount of sample which is too small is applied to the test element, then this leads to a large corruption of the analytical results because in the evaluation of the results, it is assumed that the reaction zone was adequately wetted with a certain correct amount of sample liquid. A similar problem arises when enough sample liquid has been applied to the test element but not however spread appropriately over the reaction zone. If for example a drop of blood is applied in such a manner that only a partial area of the reagent layer comes into contact with the sample then no reaction takes place in the remainder of the reagent layer. Such an application of sample therefore leads to incorrect analytical results.

In accordance with the invention, the area of the reaction zone which is evaluated is checked to ascertain whether a sufficient amount of sample liquid is present. This is done by comparing reflectance or transmission values with each other from at least two partial areas of the application zone or of the evaluation zone.

Test elements in the sense of the present invention have an application zone for sample liquid as well as one or more evaluation zones. In the most usual test strips to be available today for reflection measurements, sample liquid is applied to the application zone and permeates from there to the reagent layer. The reagent layer is usually optically accessable from the reverse side of the strip to the application zone and serves for the purposes of evaluating the test element and is therefore termed evaluation zone. Sample application and evaluation therefore is made from sides lying opposite to each other. Furthermore test elements for reflectance measurements are available in which the sample application and evaluation is performed on the same side. In this case, the application zone and the evaluation zone are identical.

In test elements suitable for transmission measurements, the side for sample application is also termed application zone. Due to the degree of transparency required of the test element, all the layers of the test element serve as the evaluation zone.

To determine whether the application zone of a test element has been evenly wetted with a sufficient amount of sample liquid, the method of the invention ascertains whether differing areas of the evaluation zone have similar transmission or reflectance characteristics. This measuring principle assumes that the sample application itself and/or a reaction product of the sample liquid together with the reagent layer leads to a change in the reflectance or transmission characteristics. If for example a colored liquid like blood is applied to a test strip then the resulting coloration allows the determination of whether different areas of the sample application zone have been wetted by the liquid. Preferably for the purposes of the determination according to the invention, a change in reflectance or transmission is utilized which occurs as a result of a reaction between the sample liquid and the reagent layer of the test element. Using test elements suitable for reflectance measurements, the determination is preferably performed on the reverse side to the sample application. This has the advantage that it is not only possible to recognize an uneven distribution of the sample but also possible flaws in the test element such as for example inconsistent permeability for the sample liquid or changing reagent concentrations in the reagent layer can be identified which would lead to an uneven coloration of the evaluation zone.

To determine whether a sufficient amount of sample liquid has been evenly applied to the sample application zone an analytical system can be used in the context of a first embodiment of the invention which has at least two sources of light capable of illuminating separate areas or at least not fully overlapping areas of the application zone or of the evaluation zone of the test element. Using at least one sensor light is detected which is reflected by the evaluation zone or which is transmitted through the evaluation zone. By examining two regions of the evaluation zone, it can be determined whether sufficiently similar signals have been received. If this is not the case, then in the area under consideration an evenly distribution of the reaction between the sample and reagent did not take place, which is because either too little sample liquid was applied or the sample liquid was not evenly applied to the application zone or the test element was defect. In each of these cases, the test element can not be properly evaluated and the user has to be made aware of this situation. If however in contrast sufficiently similar signals are received from the areas under examination and assuming that the areas were suitably selected, it can be presumed that the analysis performed was valid and is usable in a subsequent step for quantification. To facilitate the comparison of differing areas of the evaluation zone, the areas examined should not fully overlap. The areas examined may however partially overlap. Reciprocal to the procedure described, the examination of different areas of the evaluation zone can be performed using two sensors which receive radiation from differing areas of the evaluation zone.

In the first embodiment of the invention using at least two sources of light, more sources of light can be employed so that more areas of the evaluation zone can be considered. In practice, it has been discovered that with the said embodiment of the invention using two sources of light, all cases of insufficient amounts of sample applied or uneven application of sample can be detected. Analogously, this also holds true for the second embodiment of the invention using two sensors.

Sources of light in the sense of this invention are not only those with a substantially continuous emission spectrum of light, such as incandescent lamps, but also those which emit line spectra, e.g. light emitting diodes. Light emitting diodes are especially suited for application in a portable analytical system because they have a relatively high degree of efficiency which is of importance for instruments powered by batteries. Furthermore, light emitting diodes are available for a range of wavelengths in the visible region as well as in the infrared region. Preferably in an analytical system of the invention, a source of light is employed which emits the main amount of its radiation in a wavelength region which is strongly absorbed by the evaluation zone after the analyte has reacted. For a test zone, for example, which turns red after reacting with analyte, a green light emitting diode would be employed. Within the first embodiment using two or more light sources it is advantageous if the light sources have a similar spectral intensity distribution. However, on the other hand it is possible to employ light sources with different spectral intensity distributions if the evaluation unit is being calibrated respectively.

In the first embodiment, the sources of light are activated sequentially. Preferably a time of less than o.5 s elapses between the activation periods of the light source. Hereby it is being accomplished that a change in remission which is caused by color development of the reagent zone does not simulate an uneven distribution of the sample liquid.

In the first embodiment of the invention radiation reflected by the evaluation zone of the test element is detected by at least one sensor and in the second embodiment of the invention by at least two sensors. Sensors in the sense of this invention are semiconductor elements known in the prior art such as photodiodes, phototransistors or photovoltaic cells. In accordance with the second embodiment where at least two sensors are employed, it is advantageous that the sensors have a similar spectral sensitivity.

In each of the two embodiments of the invention the output signals of the sensor(s) are received by the evaluation unit and converted to measured signals. This conversion can also comprise the conversion of an analog sensor signal into a digital value. However, it is usually often necessary to convert the output signal, with consideration of instrument-specific parameters in values, which are comparable with each other. In the ideal case, in which the first embodiment of the invention possesses two sources of light of equal intensity, identical spectral intensity distribution and also the same illumination characteristics such that the areas of the application zone which are illuminated are equal in size and are illuminated with the same intensity, conversion likewise does not have to be performed when the optical path from the first source of light are the same over the distance from the application zone to the sensor and from the second source of light over the application zone to the sensor. As this ideal case however rarely occurs in practice, calibration of a given instrument should be performed at the factory and optionally before every measurement. In the first embodiment of the invention having two sources of light this can be performed such that a homogeneous test strip is illuminated sequentially with both sources of light and the output signal generated by the sensors can divided. The quotient obtained thus takes into consideration differing intensities, intensity distributions, radiation cone of the individual sensors as well as possibly differences in the light pathlengths. With the aid of the quotients so obtained, at a later point in time, signals derived from the test element to be examined can be converted into a measured value and can be compared to each other. In the most simple cases, this is performed by multiplying one of the output signals obtained by the quotient. In practice, the conversion is more complex because, for example, a dark current correction of the sensor has to be performed to compensate for stray light which does not originate from the light source as well as amplifier background noise and other electronic effects.

Besides relative correction of both sources of light against each other, an absolute calibration can be performed. For this purpose, a test element of known reflectance and transmission is sequentially illuminated with the sources of light used and a calibration factor determined which facilitates a conversion of the sensor signal to absolute reflectance or transmission values. Because the calibration procedure is performed for every source of light, a calibration factor is assigned to each one of the sources of light. Preferably the calibration is performed not only on a single test element of known reflectance and transmission but rather also on two or more with differing optical characteristics. In this procedure, two or more value pairs are obtained from the sensor signals and reflectance or transmission values for each source of light such that by using the value pairs obtained a line of calibration or a general calibration curve for the conversion of the sensor signals to reflectance values can be plotted.

In a second embodiment of the invention having at least two sensors, when the test element is illuminated, the output signals of at least two sensors is received. Calibration of such a device can be performed analogous to the described procedure for the first embodiment of the invention.

In each of the two above-named embodiments of the invention, the evaluation unit simply compares the measured values with each other and on the basis of their deviation it is determined whether the areas of the evaluation zone examined exhibit a sufficient amount of similarity with respect to their reflectance or transmission characteristics. This inspection is preferably conducted by calculating the difference between measured values determined. To facilitate the calculation of the difference, the evaluation unit contains a module for the calculation of differences which is for example realized using an operational amplifier.

The magnitude of the difference is used as a criterion to determine whether a sufficient amount of sample has been applied to the test element. The test element is identified as suitable for quantitative evaluation when the magnitude of the difference lies below a predetermined threshold. In practice however, when the evaluation zone is strongly colored greater deviations of the values measured are tolerable as is the case at lower analyte concentrations with accompanying lesser degree of coloration. For differing degrees of reflectance, advantageously differing threshold values of deviation can be employed. It is also favorable instead of the difference to use a relative deviation of the measured values to each other because in this case the absolute magnitude of the measured value is considered too and in this method the described advantages of using several threshold values in inherent. The relative deviation of the values measured can be determined by setting their differences from the mean in relation to the mean. If in the first embodiment of the invention more than two light sources are employed, then a plurality of differences between the individual measured values can be formed and their deviations from each other can be examined. The same is valid for the use of several sensors in the second embodiment of the invention.

In addition to measured value differences and a relative deviation of the measured values to each other, in accord with invention, the quotient of measured values can be formed to ascertain whether the evaluation zone is sufficiently homogeneous for the purposes of quantitative evaluation. When quotients are used as the determining criteria, an examination is made of how close the quotient is to the number one. Threshold values below or above one can be selected which may not be undercut or exceeded.

The permitted deviations of the values measured where it has been determined that the evaluation zone of the test element is sufficiently homogeneous to yield a quantitatively correct result can be determined in serial experiments. Normally, it will simply only be necessary to determine the permissible threshold values once for any given model of instrument and a given test element type. The threshold value need only be stored once in a memory in the analytical system in the form of a predetermined threshold value. It is however advantageously possible, that the usual coding of test strips also contain such threshold values. The analytical system can thus be made more flexible for various different types of test element or production-process fluctuations of the test elements.

The irradiation of the evaluation zone of the test element and detection of the transmitted or reflected radiation, preferably occurs several times on the same test strip. In such a procedure, either sample is applied to the test element and the strip is then transferred to an analytical system of the invention or the application of the sample liquid occurs when the test strip is already situated in the analytical system. The initiation of the measurement can for example be undertaken by the user by pressing a button or also by an automatic recognition of a test element in the analytical system, for example, using a light barrier or a microswitch or the like. Preferably, after initiation of the analytical system measurements are repeated at regular time intervals. The development of color in the evaluation zone can be monitored and the deviation of the measured values from each other can be tracked. If the deviation of the signals after a sufficient time interval do not fall below the set threshold value, then the test element is rejected and is not quantitatively evaluated. On the other hand it is important that evaluation does not take place prior to a change in the evaluation zone has taken place because this could simulate there being a sufficient amount of sample. Therefore it is advantageous in addition to measuring the deviations of the measured values from each other to also consider the absolute values of the individual measured values. This is performed particularly easily when the sensor signals are converted to measured values which correspond to relative or absolute reflectances or transmission values. Such measured values can, prior to the execution of the evaluation, be monitored to ascertain whether their values are constant over a given time interval on the one hand meaning that the analytical reaction is completed to a sufficient extent and whether a reaction has taken place to sufficient extent at all.

In the context of this invention, test elements can advantageously be used in which the application zone for sample liquids is covered by a net. The presence of the net means that regions of the application zone over which the sample liquid spreads is relatively sharply defined. This is due to a threshold function of the net. Because of the surface tension of the liquid in the net, a tendency exists for individual compartments of the netting to completely fill up with liquid film or not to take up any liquid at all. This all or nothing principle leads to the formation of sharp liquid leading edges along the lines of the netting which can be particularly well evaluated in a device of the invention.

Suitable nets for the covering of the sample application zones normally have square or right-angled mesh and preferably consist of a hydrophilic material which does not take up any significant amount of liquid. Suitable net materials are for example monofile, large-meshed synthetic fiber textiles made of polyester, polyamide and so on, preferably impregnated with detergents. In accord with this invention it has proven to be of advantage when the connecting lines between the illuminated areas of the evaluation zone form an angle of 45° with the fibers of the net. The same applies to the second embodiment of the invention in which connecting lines between the areas from which the sensor receives radiation form an angle of 45° with the threads of the net.

The present invention can advantageously be performed using sources of light of differing intensity distribution. In the first embodiment of the invention, sets of at least two sources of light are employed, which to all intents and purposes have overlapping spectral intensity distributions. Within each set the method of the invention can be applied whereby a comparison of the measurements yielded by the pairs gives additional certainty. Furthermore, sources of light of differing spectral intensity can also be used to enable quantitative evaluation of the test element at different wavelengths. Accordingly in the second embodiment of the invention two or more sources of light of differing spectral intensity can be used.

BRIEF DESCRIPTION OF THE DRAWINGS

This invention is illustrated in more detail using the following figures:

FIG. 12: Schematic representation of another embodiment of the invention FIG. 13: Schematic representation of a system according to yet another embodiment of the invention.

FIG. 1 depicts a schematic representation of a system according to the first embodiment of the invention. The figure shows a test element (T) with an evaluation zone (A) located on it which is illuminated by two sources of light ($L_1$, $L_2$). Each of the sources of light is focused onto the appropriate area of the evaluation zone ($B_1$, $B_2$) using a lens or a lens system. Diffuse reflected radiation from these areas is received by the detector (D) and the output signal is transferred to the evaluation unit (E). The evaluation unit determines from the output signals of the sensors whether a sufficient amount of sample has been evenly applied to the application zone of the test element by comparing the reflectance values of the areas $B_1$ and $B_2$. If the reflectance values are similar enough to each other then a corresponding message can be displayed on the display (Z). Normally, in this case a quantitative evaluation of the test element can be directly made. If the difference between the reflectance values obtained from the areas $B_1$ and $B_2$ exceed the predetermined threshold value then an appropriate message is displayed on the display (Z).

In order to determine whether a sufficient amount of sample liquid has been evenly applied, a control unit (S) first of all activates the light source $L_1$ and simultaneously transfers the information to the evaluation unit that the incoming output signal of the sensor stems from light source $L_1$. After the light source $L_1$ is deactivated, the procedure is repeated using light source $L_2$. On the basis of the output signal obtained, the determination is made in the manner already described after conversion to measured values. For a possible subsequent quantitative evaluation of the test element, the light sources can be activated one after another and either the measured value or the concentration values which they yield can be used to calculate an average value. Furthermore, the light sources $L_1$ and $L_2$ can be activated such that the output signals received by the detector can be evaluated. For this subsequent measurement a further source of light can be used which preferably illuminates a smaller area of the evaluation zone (A) than the light sources $L_1$ and $L_2$. In accord with the invention it is however advantageous to undertake the evaluation using the light sources $L_1$ and $L_2$ because this means that no further light sources have to be integrated into the analytical system and furthermore areas $B_1$ and $B_2$ have been verified to contain enough sample liquid. In this method usually only a relatively small part of the evaluation zone is used and information from other areas of the evaluation zone is not considered but however for all intents and purposes one can exclude the possibility that false information from areas other than $B_1$ and $B_2$ is considered in the evaluation step.

Figure 2:
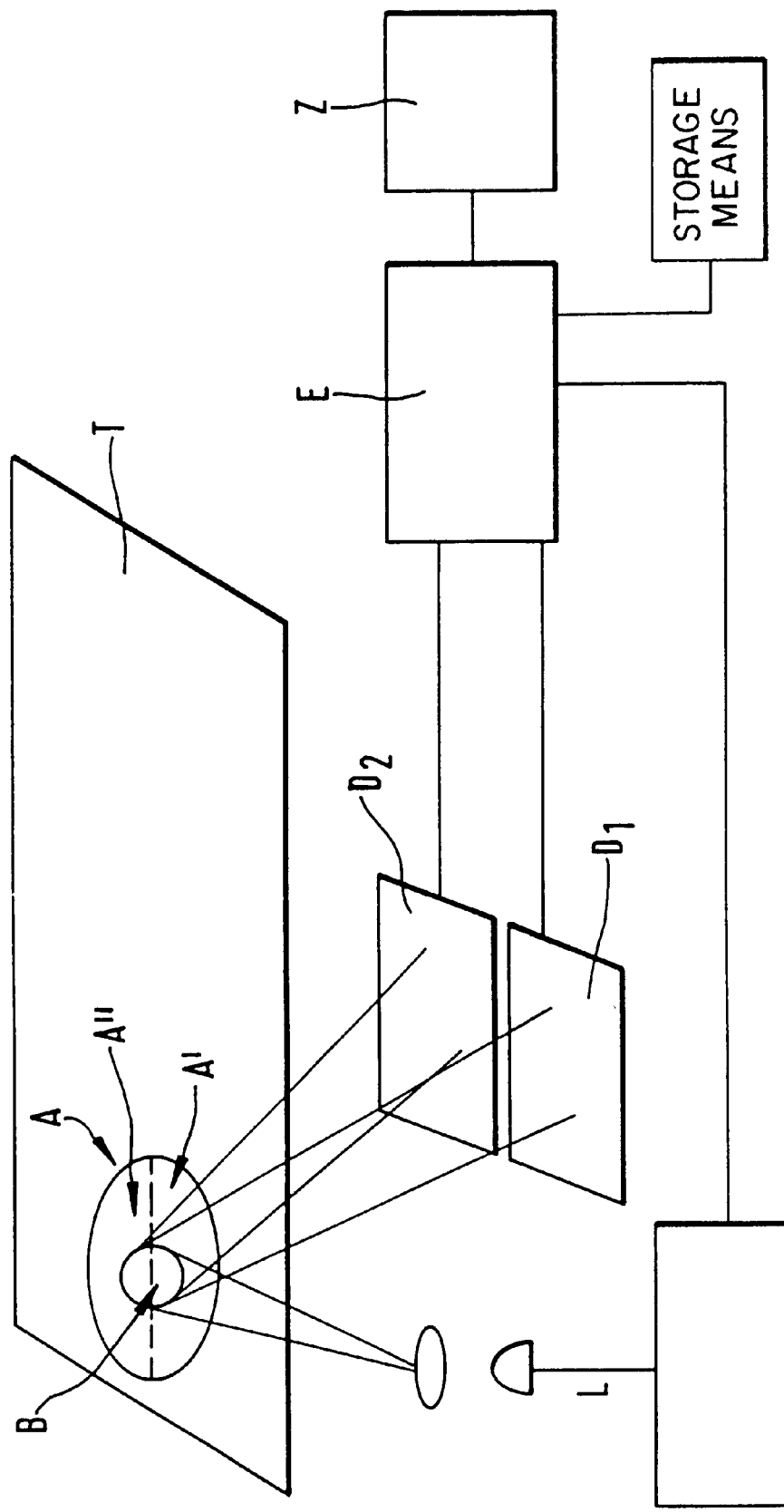
FIG. 2: Schematic representation of a system according to embodiment 2

FIG. 2 schematically represents a device in accordance with the second embodiment of the invention. A light emitting diode (L) illuminates an area (B) of the evaluation zone (A) of the test element (T) through a lens or a lens system. Radiation reflected by the evaluation zone is transferred by the detectors $D_1$ and $D_2$ to the evaluation unit (E). Due to the geometrical arrangement, the detector $D_1$ receives a greater signal from area A' of the evaluation zone than from area A". In contrast the detector $D_2$ receives a greater signal from the area A" than from the area A'. The output signals from the detectors are converted by the evaluation unit (E) into measured values and it determines whether the magnitude of the difference of the measured values is smaller than the prescribed threshold value. The evaluation unit (E) is coupled with the control unit (S) which controls the source of light (L). This guarantees that the evaluation unit receives the signals from the detectors while the light source is activated. The results of the evaluation can be displayed on the display unit (Z) which is in turn connected to the evaluation unit.

Figure 3:
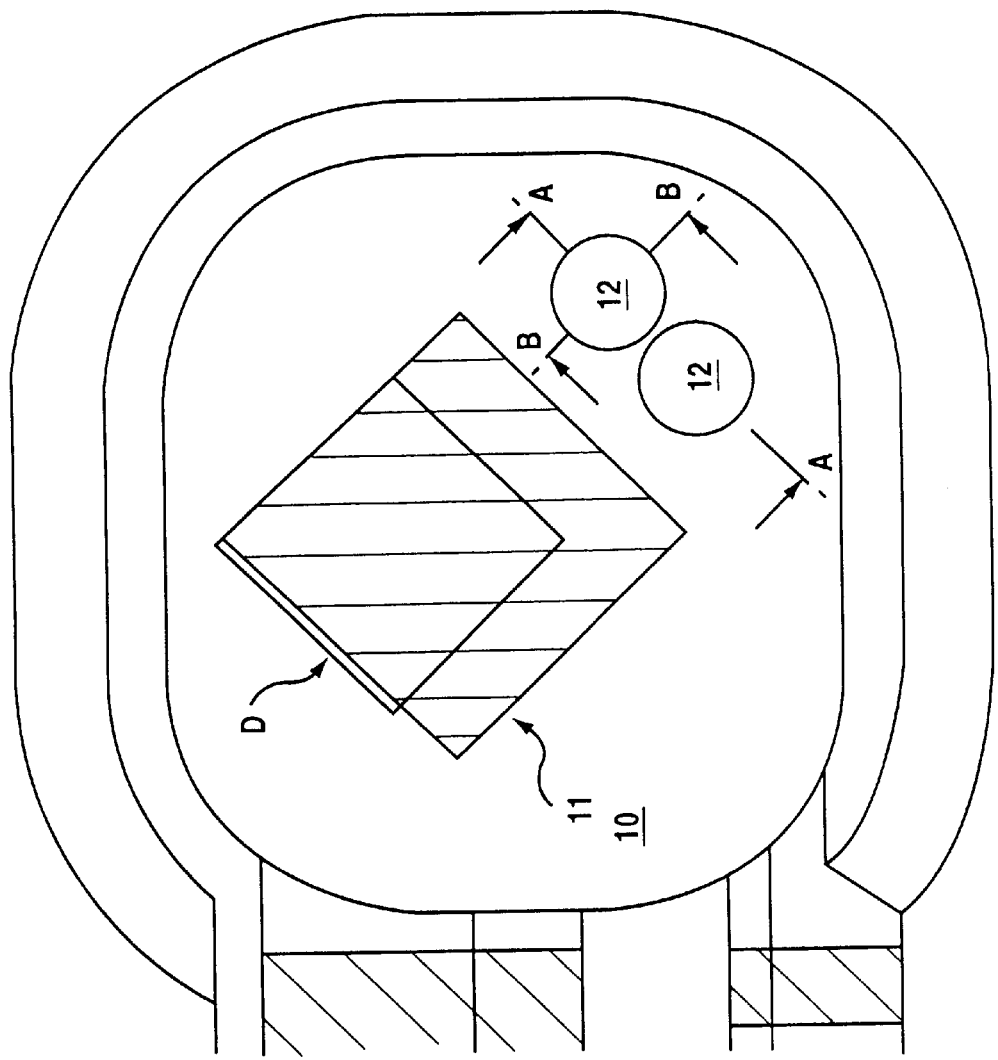
FIG. 3: Top view of the cover for the optics of an analytical system according to embodiment1

FIG. 3 is a top view of a cover (10) of the measuring area of the analytical system. The cover (10) is comprised of a black, light-absorbing plastic. An optical window (11) made of plastic is located in it under the detector (D). In vicinity to an edge of the detector (D), two lenses (12) are depicted through which light (from the light sources lying below) can shine onto the evaluation zone. In FIG. 3 a cross-hatched pattern on the optical window (11) signifies how the net lines of a test element are projected onto the detector. It can be recognized that net lines between the connecting line A—A which runs between the optical lenses (12) (and therefore also runs between the sources of light) form an angle of 45°.

Figure 4:
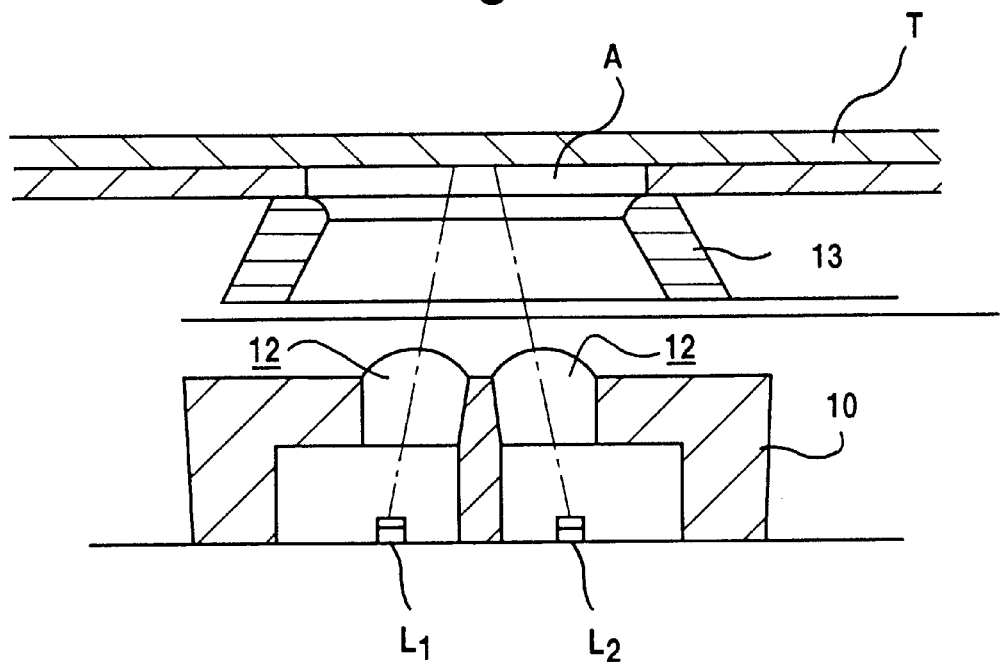
FIG. 4: Cross-section through FIG. 3 along the line A—A

FIG. 4 is a cross-section of the analytical system of FIG. 3 taken along the cut-line A—A. In this illustration the arrangement of the light sources ($L_1$, $L_2$) relative to the optical lenses (12) as well as the test strip (T) can be clearly seen. The sources of light are located below the optical lenses (12) which are located in the cover (10). In the case illustrated, the lenses are made out of a transparent plastic such as for example polymethacrylate. The sources of light illustrated are light emitting diodes with a light emitting level having the dimensions of 0.2×0.2 mm. A test strip surface (13) is located above the cover (10) which is conical in shape and tapers in the direction of the evaluation zone (A) of the test element (T).

Figure 5:
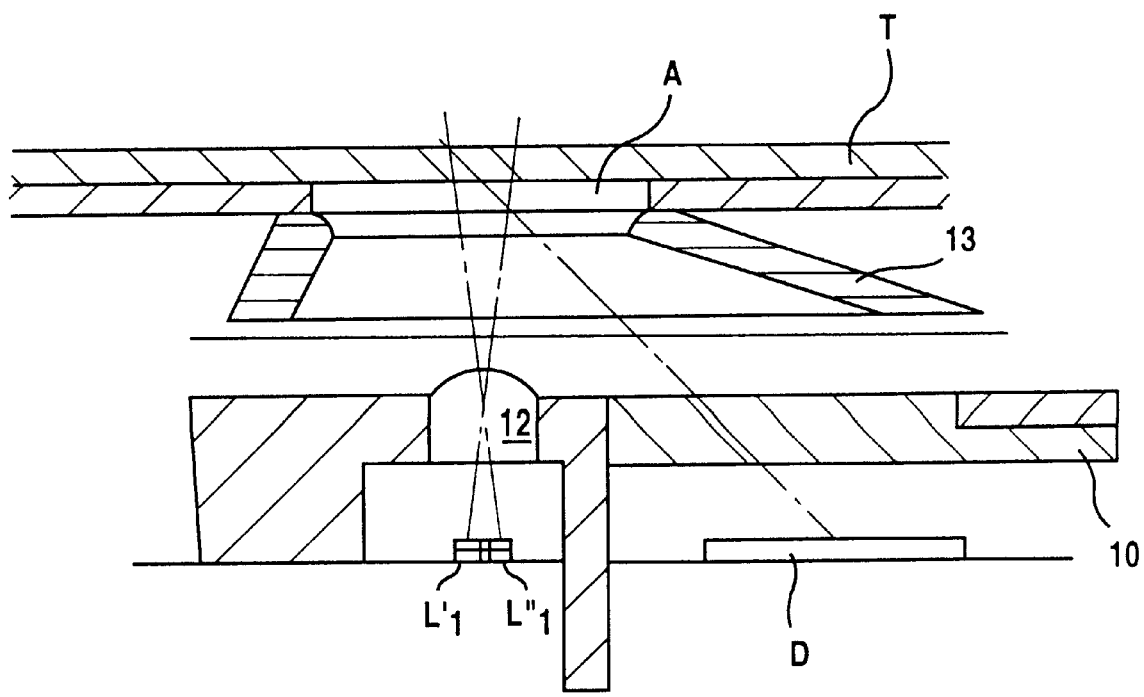
FIG. 5: Cross-section of FIG. 3 along the line B—B

FIG. 5 illustrates a cross-section through FIG. 3 along the line B—B. In this view it is possible to observe that two light emitting diodes are arranged juxtapose below every optical lens. In this prefered embodiment of the invention it is possible to save space by not using additional optical elements (lenses) to house two sets of two types of light emitting diodes each. The first light emitting diode displayed in FIG. 5 ($L_1$') emits mainly in the green region, whereas the second light emitting diode ($L_1$") emits mainly in the red region of the electromagnetic spectrum. It can also be seen from FIG. 5 that the test strip bed (13) has a geometrical form which allows as much light reflected from the evaluation zone (A) to fall onto the detector (D) as possible. The dimensions in mm detailed in FIG. 5 also illustrate how very much an analytical system according to the invention can be miniaturized.

Figure 6A:
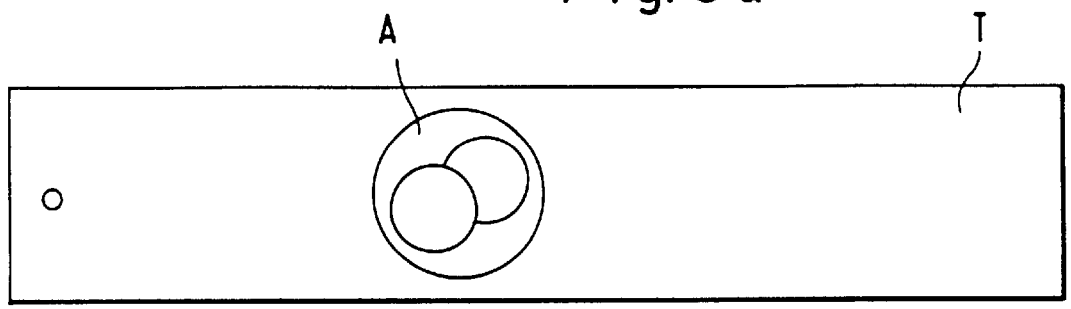
FIGS. 6a and 6b: Representation of the illuminated areas of the test element
Figure 6B:
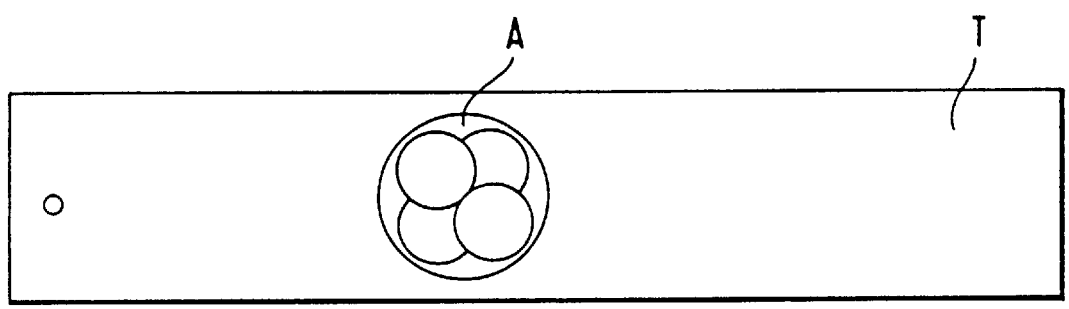

FIGS. 6a and 6b illustrates upper sides of two test elements and their evaluation zones (A). The circles detailed on the evaluation zones denote regions which are illuminated by the light and the lens system. Two circle shaped regions in FIG. 6a are illuminated in the upper test elements which completely lie within the evaluation zone and overlap only to a small extent. It is of advantage in the sense of this invention when the overlap of the illuminated areas amounts to less than 50% of the surface of a single light spot. Furthermore one can recognize that the total illuminated surface is larger than the non-illuminated area which is also of advantage in practice. Viewing FIG. 3 and FIG. 6a together one can see how a test element is arranged relative to the source of light during a measurement.

In the lower region of FIG. 6b a test element is displayed in which the evaluation zone is illuminated by four different sources of light of approximately the same wavelength. This pattern of illumination can be generated by four sources of light arranged in an approximately quadratic manner. As already mentioned the use of a larger number of sources of light makes the recognition of too low a quantity of sample or defect test strips more certain, especially when the sample application zone is not covered by a net.

Figure 7A:
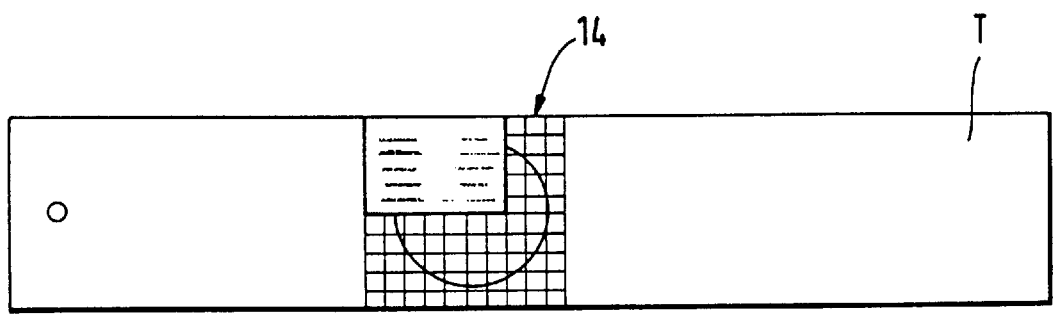
FIGS. 7a and 7b: Test strip with sample applied from above (application zone) and below (evaluation zone)

FIG. 7a illustrates the upper side of a test element which can be used to advantage in an analytical system of the invention. The sample application zone is covered with a net (14) which has square meshing. In the upper left area of the sample application zone, a gray area is illustrated which shows in an exemplary fashion how a sample liquid applied spreads out.

Figure 7B:
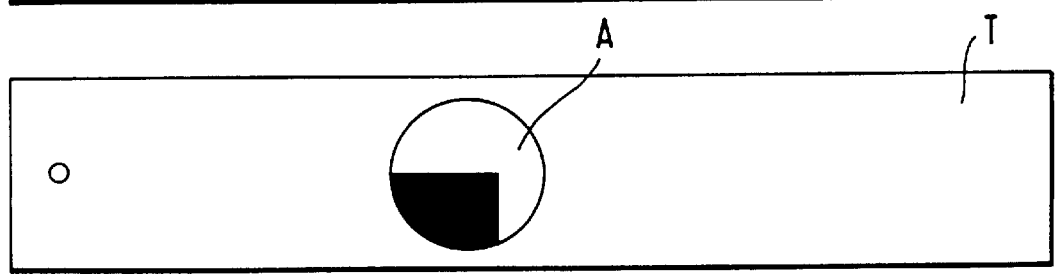
Figure 8:
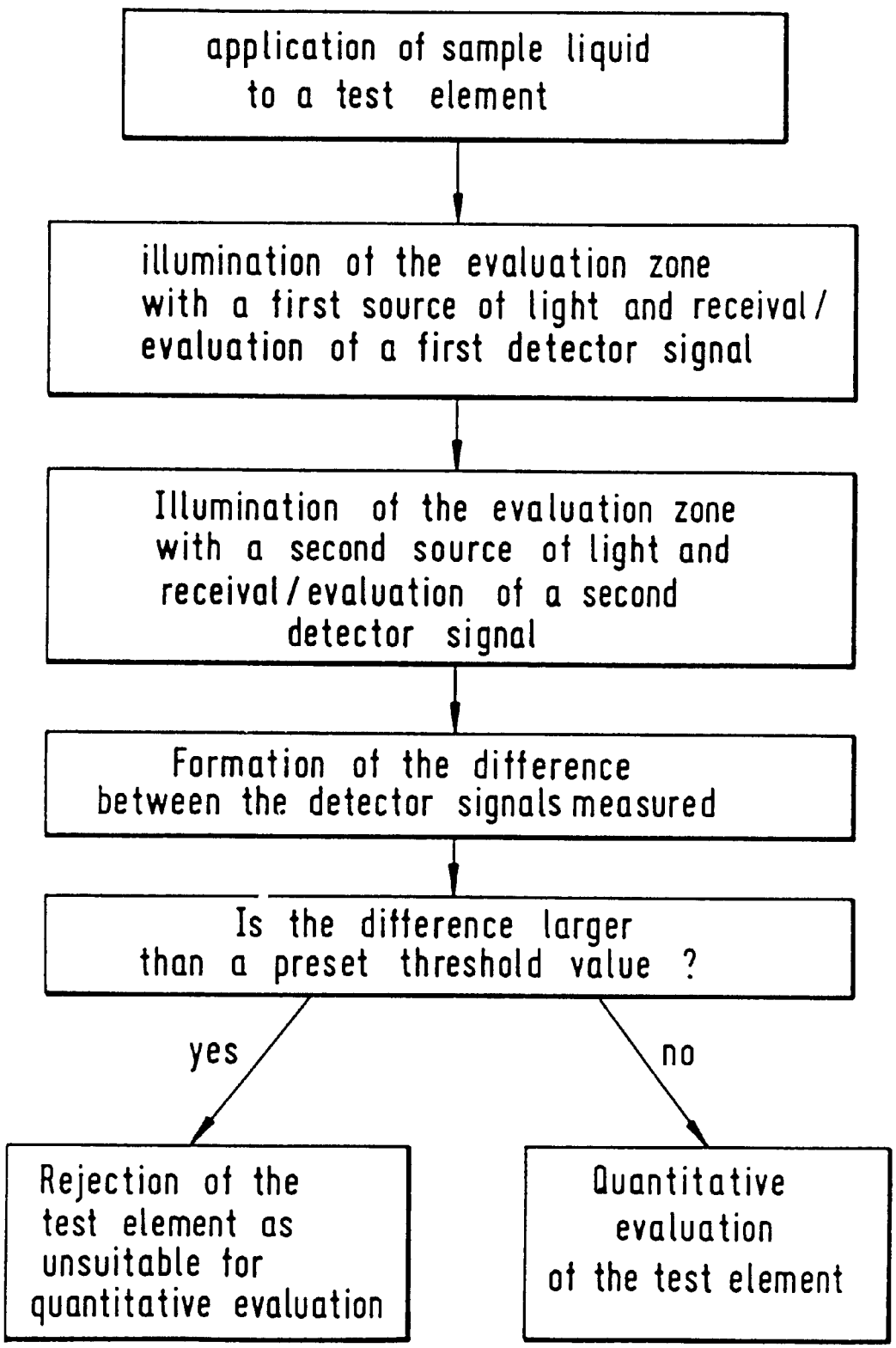
FIG. 8: Procedural steps for determining whether a sufficient amount of sample liquid has been evenly applied to the application zone of a test element

FIG. 7b illustrates the same test element from the reverse, lower side. The test element carrier material is provided with a circular opening through which the evaluation zone is optically accessible. The application of sample liquid generates a coloration of the evaluation zone which is depicted by a black circle segment.

Figure 9:
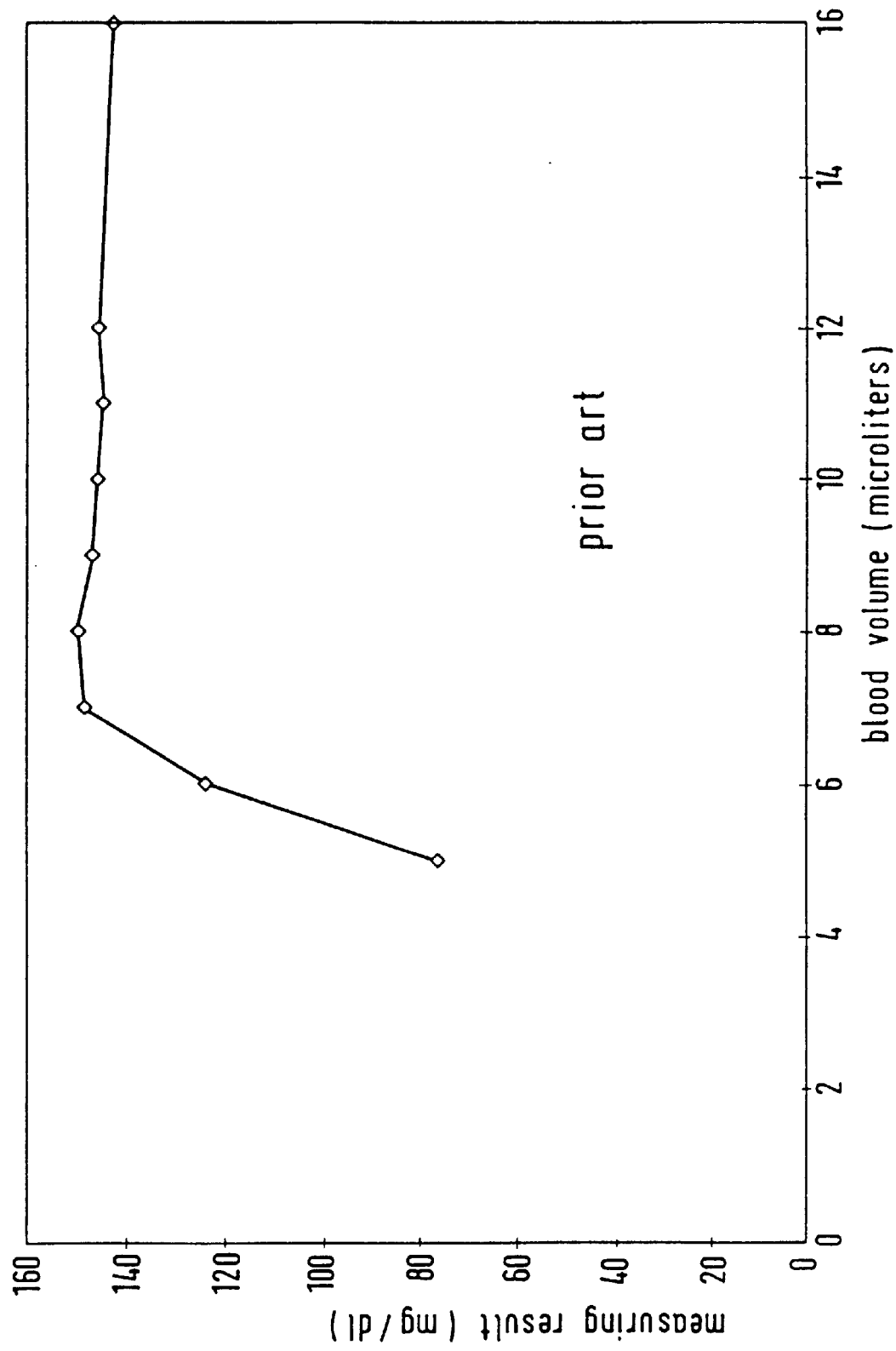
FIG. 9: Evaluation curve for different volumes of blood using standard technology blood glucose analyzers and test elements

FIG. 9 illustrates a curve for blood glucose determinations which was obtained using prior art analytical systems and suitable test elements. The sample liquid was a blood sample with 150 mg/dl glucose. The amount of sample volume applied to the test element (in μl) is displayed along the X-axis in FIG. 9. The Y-axis shows the result of the analysis in mg/dl glucose. One can see from the shape of the curve that sample volumes below 8 µl give rise to false results.

Figure 10:
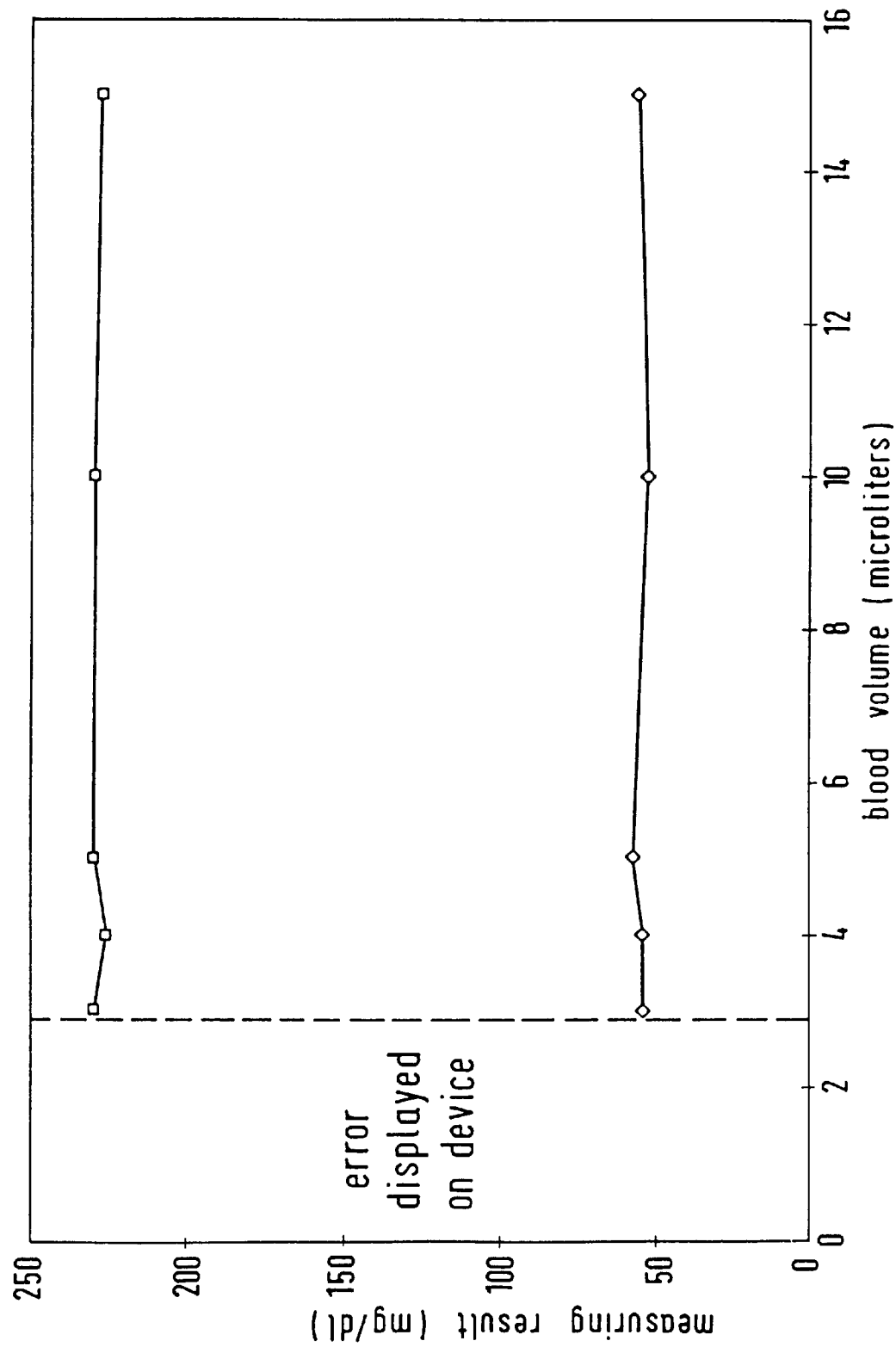
FIG. 10: Resulting curve derived using a blood glucose analyzer and an evaluation unit in accord with the invention

FIG. 10 illustrates a similar series of experiments using the analytical system of the invention. The upper curve was derived from a drop of blood containing 230 mg/dl and the lower curve from a sample containing 50 mg/dl of glucose. The greater accuracy of the analysis results below 8 µl are due to an improved test element. FIG. 10 illustrates however that the instrument does not supply results for an amount under 3 µl but rather gives an error warning. This ensures that the application of too small a volume of sample to the test element does not give rise to a false reading.

Figure 1:
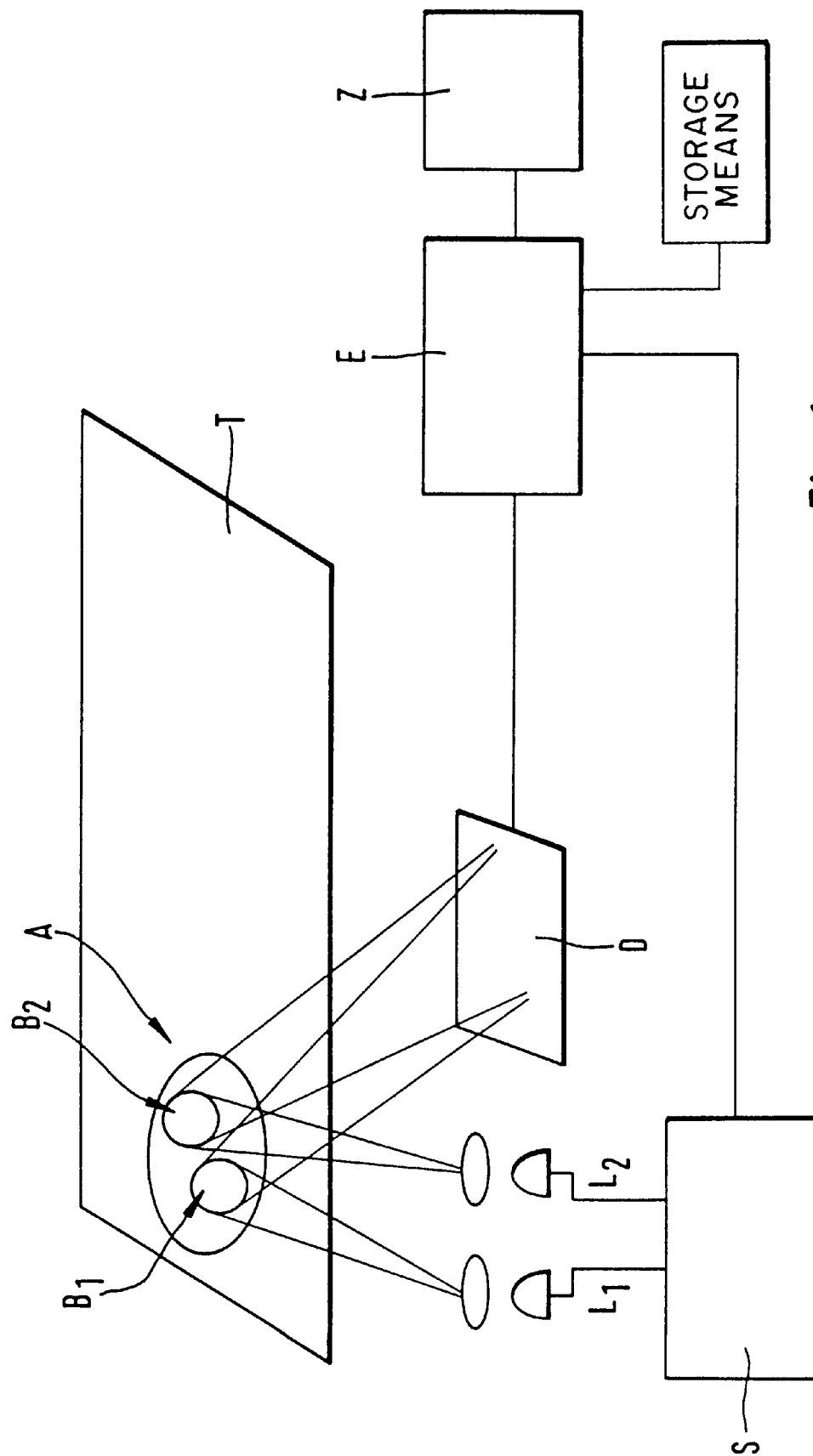
FIG. 1: Schematic representation of a system according to embodiment 1
Figure 11:
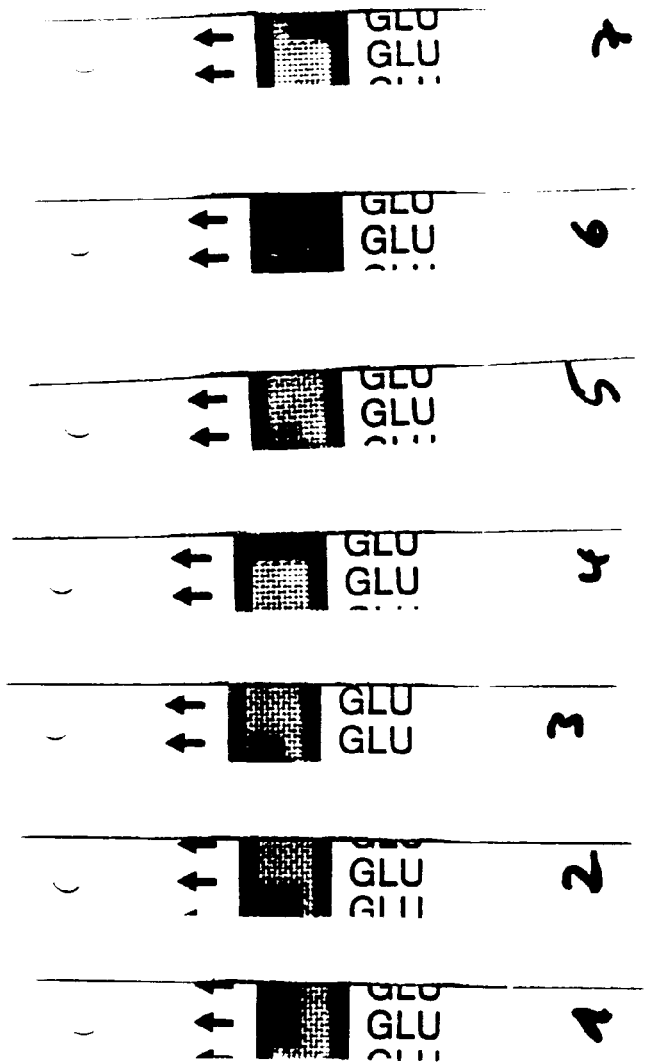
FIG. 11: Photographs of test elements having sample applied to hereon

FIG. 11 displays pictures of real test elements which were evaluated in an analytical system of the invention. The following results were obtained:

FIG. 12 illustrates an embodiment of the invention similar to the embodiment shown in FIG. 1. In FIG. 12, however, it can be seen that light is shown as being transmitted through illumination areas $B_1$ and $B_2$.

FIG. 13 is comparable to the embodiment of FIG. 2, but illustrates a configuration wherein light emitting diode L transmits light through illumination area B of evaluation zones A' and A", onto detectors D1 and D2. A difference in the output signals of the detectors is used for evaluation, as discussed previously. The light transmitted through the illumination areas in FIGS. 12 and 13 is secondary light.

FIGS. 12 and 13 illustrate a storage device or storage means connected to evaluation means E. The storage device stores calibration factors therein, and evaluation unit E converts the output signal into the measured value utilizing the calibration factors stored in the storage device.

TABLE 1

| Test element No. | 1 | 2 | 3 | 4 | 5 | 6 | 7 |
|---|---|---|---|---|---|---|---|
| Relative reflectance 1 | 80% | 85.8% | 98.1% | 94.4% | 99.2% | 31.5% | 94.7% |
| Relative reflectance 2 | 42.3% | 46.7% | 84.0% | 98.7% | 95.4% | 31.6% | 98.2% |
| Difference between reflectance values | 37.7% | 39.1% | 14.1% | −4.3% | 3.8% | −0.1 | −3.5% |

The reflectances listed in the above table are relative reflectances compared to a dry test strip whose reflectance was set at 100%. It can be seen from the table that test elements (1 to 3) which are inhomogeneously wetted with sample can be identified clearly. In the inhomogeneously wetted test elements 5 and 7, the differences between the measured reflectances is relatively small with due to the fact that sample wetting runs along a diagonal line of the evaluation from the upper left to the lower right in a symmetrical fashion. Due to the fact that the measurements in Table 1 were yielded by an analytical system according to FIGS. 1 and 3, the illuminated areas were ordered along the designated diagonals from the upper left to the lower right and were able only to recognize the low-dosage with difficulty. The test elements 5 and 7 were purposefully wetted in this symmetrical fashion to test the limits of the method. Such symmetrical wetting occurs very rarely in actual practice.

The test element (6) in FIG. 11 exhibits only a very small difference between measured reflectance values because it is homogeneously wetted in an ideal way. Because of the approximate similarity of the relative reflectances to the first significant figure after the decimal point, one can ascertain to what level of accuracy the reflectances were determined and can be compared with each other. Selecting the threshold value for the difference of the reflectances (preferably less than 2% reflectance), inhomogenously wetted test elements can be recognized with certainty.

| List of Reference Numerals | |
|---|---|
| A: | evaluation zone |
| T: | test element |
| $B_1$, $B_2$: | illuminated areas |
| L, $L_1$, $L_2$: | light sources |
| S: | control unit |
| D, $D_1$, $D_2$: | detectors |
| E: | evaluation unit |
| Z: | display |
| (10) | cover |
| (11) | optical window |
| (12) | optical lens |
| (13) | test strip bed |
| (14) | net |

We claim:

1. An analytical system for evaluation of test elements, said analytical system determining consistent application of a sufficient amount of sample liquid, said system comprising:

a first light source for illuminating a first illumination area of a sample application area of the test element;

a second light source for illuminating a second illumination area of the sample application area of the test element, said first and second illumination areas being different from each other;

control means coupled to said first and second light sources, said control means for separately controlling light irradiation from said first and second light sources;

sensor means for sensing secondary light after light from said first and second light source impinges upon the test element, said sensor means generating first and second output signals proportional to an intensity of secondary light provided by the first and second light sources, respectively;

evaluation means coupled to said sensor means, said evaluation means receiving the first output signal of the sensor and converting the first output signal to a first measured value when the first light source is activated, said evaluation means receiving the second output signal of the sensor means and converting the second output signal to a second measured value when the second light source is activated, said evaluation means comparing the first and second values and determining a deviation between the measured values, wherein said evaluation means compares the deviation value to a predetermined threshold value to determine consistent application of the sample liquid.

2. An analytical system as recited in claim 1, wherein said secondary light is light which has been transmitted through the first and second illumination areas.

3. An analytical system as recited in claim 1, wherein said secondary light is light from said first and second light sources which has been reflected from the first and second illumination areas of the sample application area.

4. An analytical system as recited in claim 1, wherein the deviation of the first and second measurement values is determined by said evaluation means based upon a calculation of the difference between the first and second measured values, with said difference being compared to the predetermined threshold value.

5. An analytical system as recited in claim 1, wherein the deviation between the first and second measured values is determined by the evaluation means as a relative deviation, said relative deviation then being compared to the predetermined threshold value.

6. An analytical system as recited in claim 1, further comprising display means connected to said evaluation means, said display means displaying an error message when the deviation between the first and second measured values exceeds the predetermined threshold value, and displaying an analytical result when the deviation between the first and second measured values is smaller than the predetermined threshold value.

7. An analytical system as recited in claim 1, wherein the secondary light detected by the sensor means is diffuse reflected light being diffusely reflected by said first and second illumination areas.

8. An analytical system as recited in claim 1, wherein said first and second illumination areas are separate from each other.

9. An analytical system as recited in claim 1, wherein said first and second illumination areas on said test element include a common part of the sample application area.

10. An analytical system as recited in claim 1, wherein the first and second illumination areas are equal in size.

11. An analytical system as recited in claim 1, wherein the first and second light sources are disposed in a coplanar relationship on a plane which is parallel to a plane of the sample application areas of the test element.

12. An analytical system as recited in claim 1, wherein the first and second light sources have substantially identical spectral intensity distributions and radiation cones.

13. An analytical system as recited in claim 1, wherein a first light path defined between the first light source, the first illumination area, and the sensor means is a mirror image of a second light path between the second light source, the second illumination area, and the sensor means.

14. An analytical system as recited in claim 1, wherein the sample application area comprises a net.

15. An analytical system as recited in claim 14, wherein said net comprises a rectangular mesh.

16. An analytical system as recited in claim 14, wherein a connecting line between a center of the first and second illumination areas of the evaluation zone forms an angle of 45° with threads of the net.

17. An analytical system as recited in claim 1, wherein said sensor means receives said secondary light from the first and second illumination areas with a same angle of incidence relative to the sample application area, and with a same distance from the first and second illumination areas.

18. An analytical system as recited in claim 1, wherein said first and second light sources and said sensor means are configured to perform quantitative evaluation of the test element.

19. An analytical system as recited in claim 1, comprising two first light sources and two second light sources, thereby forming a first set and a second set of light sources, said first set of light sources having differing spectral intensity distributions from said second set of light sources.

20. An analytical system as recited in claim 1, further comprising storage means connected to said evaluation means, said storage means for storing calibration factors therein, wherein said evaluation means converts the first output signal into the first measured value utilizing the calibration factors stored in the storage means.

21. An analytical system for evaluation of test elements, said analytical system determining consistent application of a sufficient amount of sample liquid, said system comprising:

a light source for illuminating an illumination area of a sample application area of the test element;
a first sensor means for detecting secondary light along a first light path after light from said light source impinges upon the illumination area, said first sensor means generating a first output signal proportional to an intensity of the secondary light along a first light path;
a second sensor means for detecting secondary light along a second light path after light from said light source impinges upon the illumination area, said second sensor means generating a second output signal proportional to an intensity of the secondary light along a second light path;
evaluation means coupled to said first and second sensor means for converting said first output signal to a first measured value and for converting said second output signal to a second measured value, said evaluation means comparing the first and second measured values to determine a deviation therebetween.

22. An analytical system as recited in claim 21, wherein said secondary light detected by said first and second sensor means is light which has been transmitted through said illumination area of said sample application area.

23. An analytical system as recited in claim 21, wherein said secondary light detected by said first and second sensor means is light which is reflected by said illumination area of said sample application area.

24. A method of determining consistent application of a sufficient amount of sample liquid on a test element, said method comprising the steps of:

applying a sample liquid to a sample application area of the test element;
irradiating light from a first light source onto a first illumination area of the sample application area;
detecting secondary light after light from the light source impinges upon the first illumination, thereby generating a first output signal;
irradiating a second illumination area of the sample application area with light from a second light source, said second illumination area being a different area from said first illumination area;
detecting secondary light from said second light source after the light from the light source impinges upon the illumination area, thereby generating a second output signal;

converting said first and second output signals into first and second measured values; and comparing the first and second measured values to determine a deviation between the measured values.

25. A method as recited in claim 24, wherein said detection steps are performed with a same sensor means.

26. A method as recited in claim 24, wherein said first light source and said second light source are sequentially activated.

27. A method as recited in claim 24, wherein, prior to said step of applying the sample liquid to the sample application area, a series of exposure, detection, conversion and comparison steps are performed to generate factors for converting the first and second output signals.

28. A method as recited in claim 24, wherein, prior to the step of applying a sample liquid to the sample application area, a series of exposure and detection steps are performed on a homogeneous surface thereby generating calibration output signals, and wherein a quotient from the calibration output signals is calculated and used for the conversion of the first and second output signals into the first and second measured values.

29. A method as recited in claim 24, wherein a time between the exposure of the first illumination area and the exposure of the second illumination area is less than 0.5 seconds.

* * * * *